(12) United States Patent
Dennin et al.

(10) Patent No.: US 7,179,460 B2
(45) Date of Patent: Feb. 20, 2007

(54) BACTERIAL COMPOSITION AND ITS USE

(75) Inventors: Véronique Dennin, Villeneuve d'Ascq (FR); Gregory John Leyer, Madison, WI (US); Annick Mercenier, Epalinges (CH); Sophie Nutten, Steenvoorde (FR); Bruno Pot, St-Michiels Brugge (BE)

(73) Assignee: Danisco A/S (DK)

( * ) Notice: Subject to any disclaimer, the term of this patent is extended or adjusted under 35 U.S.C. 154(b) by 264 days.

(21) Appl. No.: 10/310,549

(22) Filed: Dec. 5, 2002

(65) Prior Publication Data

US 2004/0110270 A1 Jun. 10, 2004

(51) Int. Cl.
*A01N 63/00* (2006.01)
*C12N 1/20* (2006.01)

(52) U.S. Cl. .................. 424/93.3; 435/42; 435/252.1; 435/252.9; 435/822; 435/853; 435/854; 435/857; 424/93.4; 424/93.45

(58) Field of Classification Search ................. 435/42, 435/252.1, 822, 853, 854, 857, 252.9; 424/93.3, 424/93.4, 93.45
See application file for complete search history.

(56) References Cited

U.S. PATENT DOCUMENTS

2002/0006432 A1* 1/2002 Collins et al. .............. 424/439

* cited by examiner

*Primary Examiner*—Herbert J. Lilling
(74) *Attorney, Agent, or Firm*—Fay, Sharpe, Fagan, Minnich & McKee, LLP

(57) ABSTRACT

The subject of the present invention is a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802. An other subject of the invention is an immunomodulation method comprising the step of using the at least one strain selected from the preceding group.

18 Claims, 3 Drawing Sheets

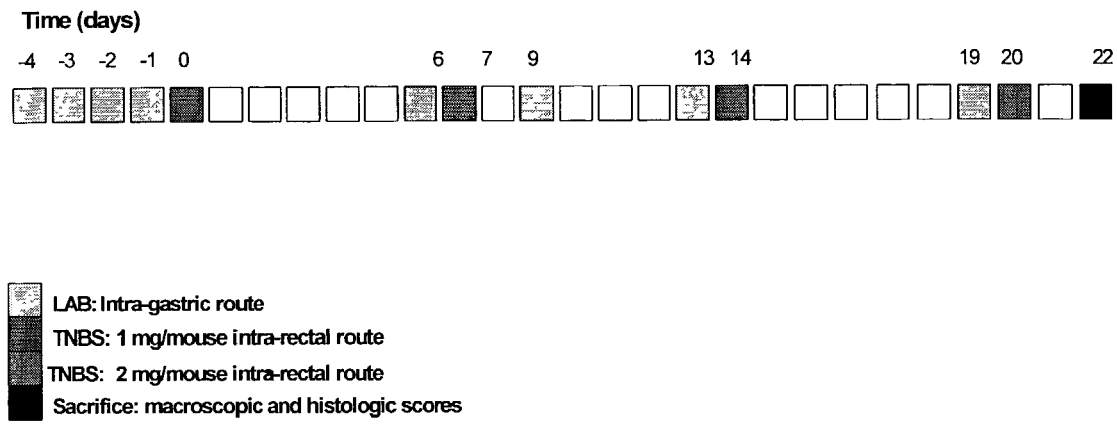
Figure 1: schedule of probiotic administration
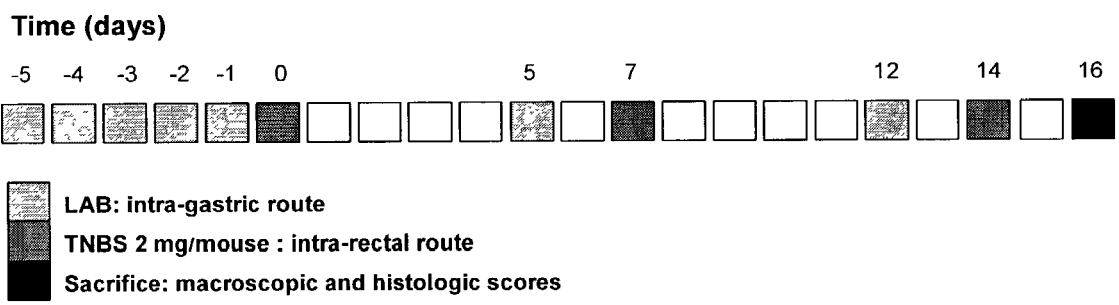
Figure 3: schedule of probiotic administration
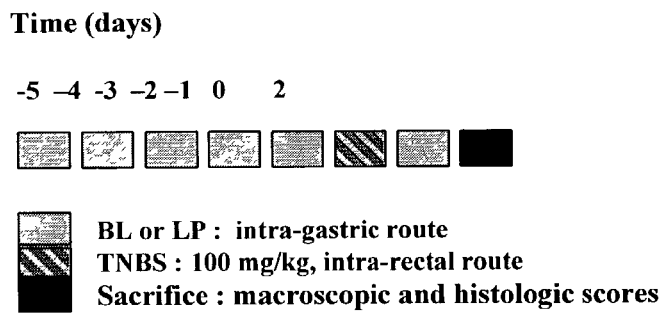
Figure 5: schedule of probiotic administration

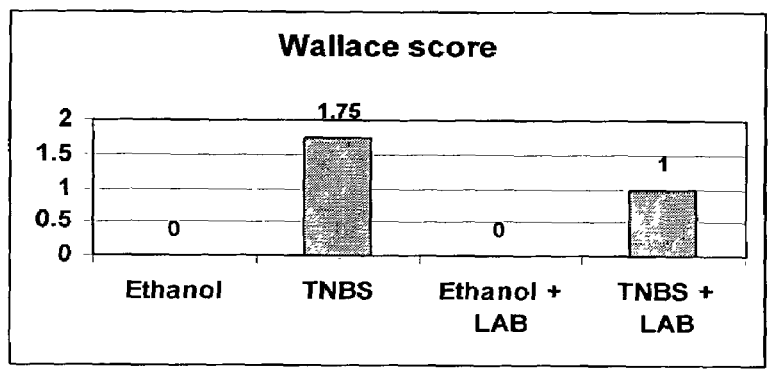
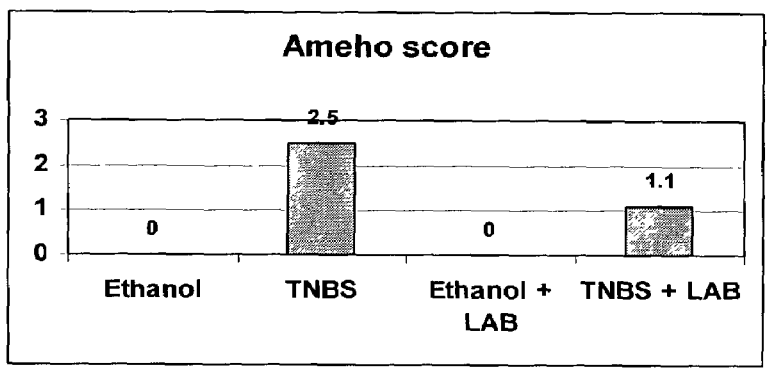
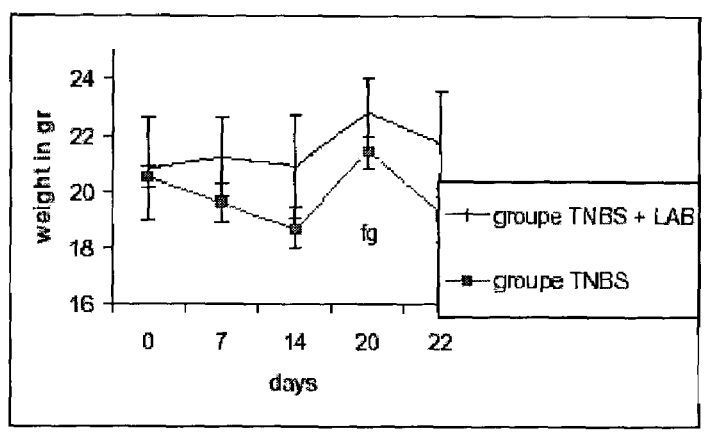
Figure 2: Wallace and Ameho scores, and weight evolution

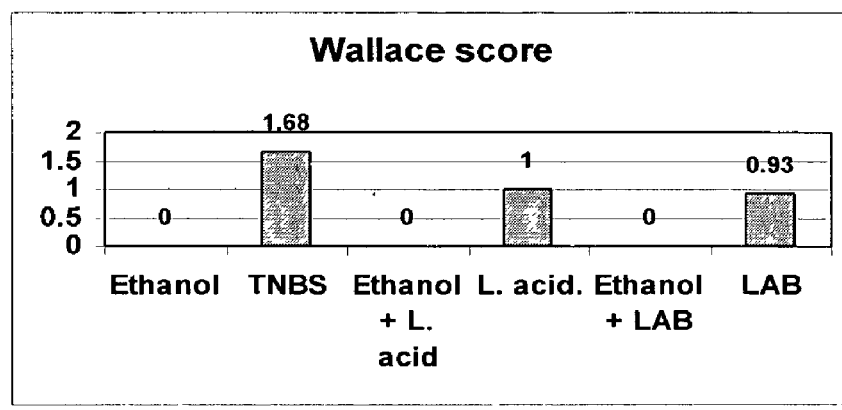
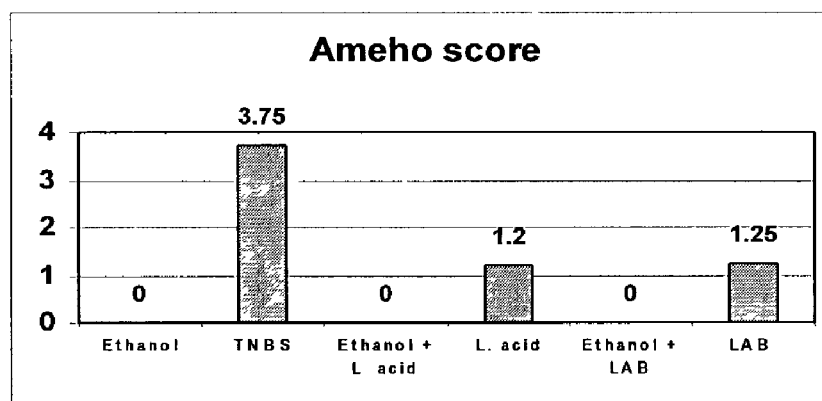
Figure 4: Wallace and Ameho scores
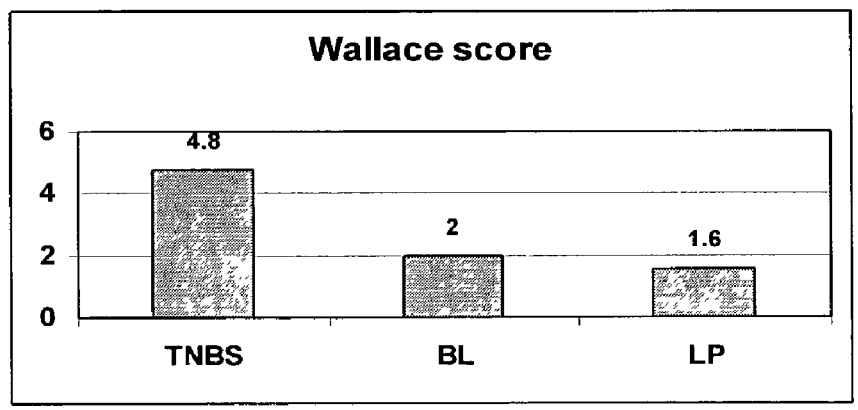
Figure 6: Wallace scores

BACTERIAL COMPOSITION AND ITS USE

The subject of the present invention is a bacterial composition, an immunomodulation method and the use of this composition. Immunomodulation is the capacity to improve the global immune functions either in healthy or in pathologic situations.

Among bacteria, some have a positive influence on the immune system of the intestinal medium, in particular lactic acid bacteria and bifidobacteria, and are termed "probiotic" bacteria or strains.

The expression probiotic bacteria or strains is understood to mean a strain which, when ingested live, exerts a beneficial effect on the host by having an action on the balance of the intestinal flora. These probiotic strains have the capacity to survive following passage across the upper part of the digestive tube. They are non-pathogenic, non-toxic and exert a beneficial action on health through in one hand their ecological interactions with the resident flora of the digestive tract and in the other hand their ability to positively influence immune system, through their effects onto the GALT (gut associated immune tissue). According to the probiotic definition, those bacteria when given in sufficient numbers have the capacity to transit alive all along the gut. There they become part of the resident flora for the period of administration. The so called colonisation (or transcient colonisation) allow the probiotic bacteria to exert beneficial effect, such as repression of potentially pathogen microorganisms on the flora and interactions with the gut immune system.

The probiotic strains most widely used, in particular in dairy products, are mainly bacteria and yeasts, of the following genera *Lactobacillus* spp, *Streptococcus* spp, *Enterococcus* spp and *Bifidobacterium* spp and *Sacharomyces* spp. Among the probiotic effects reported for those bacteria, one can cite for example, improvement of lactose tolerance, prevention and or treatment of gastrointestinal and urogenital infections, reduction of some cancers, decrease of blod cholesterol. However, it should be highlighted that not all the individual strains from the genera described above have those effects, but only some carefully selected strains do.

Thus in order to satisfy the requirements for performant probiotic strains, it has become necessary to select strains or a mixture thereof which is efficient and which allow stimulation of the immune system (immunomodulation).

Accordingly, the problem which the present invention proposes to solve is to provide a bacterial composition having probiotic properties.

The aim of the present invention is to satisfy these requirements.

For this purpose, the present invention provides a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

Another subject of the invention is an immunomodulation method.

The subject of the invention is also a food or pharmaceutical composition comprising the bacterial compositions described above.

Another subject of the invention is also the use of this composition in the preparation of a carrier administered to humans or to animals for a therapeutic or prophylactic purpose in the gastrointestinal system.

The composition of the invention has the advantage of providing unquestionable virtues which enrich the range of available strains.

Such a composition is particularly advantageous when it is administered to humans or to animals for a therapeutic or prophylactic purpose in the gastrointestinal system, in particular in the reduction of inflammatory and/or allergic reactions.

The advantage of the present invention is also to preserve all its properties when it is incorporated into a pharmaceutically acceptable carrier or into a food product.

Other advantages and characteristics of the present invention will emerge more clearly on reading the description and the examples given purely by way of illustration and without limitation, which follow.

First of all, the subject of the invention is a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

The *Lactobacillus acidophilus* used according to the invention is a Gram-positive strain. Advantageously, it is a catalase-negative strain, with a homofermentative metabolism giving rise to the production of lactic acid.

The *Lactobacillus acidophilus* used according to the invention may also produce a bacteriocin, lactacin, which is active against other microorganisms.

Preferably, it is a *Lactobacillus acidophilus* exhibiting good resistance to pepsin, under acidic pH conditions (about at least 73% of the bacteria are still alive after 40 minutes of treatment).

More particularly, the *Lactobacillus acidophilus* used according to the invention exhibits a very good resistance to pancreatin (at least 100% of the bacteria are still alive after 40 minutes of treatment).

Advantageously, the *Lactobacillus acidophilus* used according to the invention exhibits good tolerance to bile salts.

Preferably, a *Lactobacillus acidophilus* described as being "hydrophobic", that is to say which exhibits a high affinity for hydrophobic organic solvents, polar or not polar, such as for example n-decane, chloroform, hexadecane or xylene, will be used.

The *Lactobacillus acidophilus* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), γ-interferon (γ-IFN) and tumour necrosis factor α (TNFα). On the other hand, the *Lactobacillus acidophillus* used according to the invention induces little or no secretion of interleukins 12 (IL12) using this same test.

The *Lactobacillus acidophilus* used according to the invention is *Lactobacillus acidophilus* PTA-4797. This *Lactobacillus acidophilus* strain was deposited according to the Treaty of Budapest at the American Type Culture Collection where it is recorded under the deposit number PTA-4797.

One embodiment of the composition according to the invention is a bacterial composition comprising *Lactobacillus acidophilus* PTA-4797.

The composition made of probiotic bacteria according to the invention may also comprise at least one *Lactobacillus plantarum* strain.

The *Lactobacillus plantarum* strain used according to the invention is preferably a Gram-positive strain. Advantageously, it is a catalase-negative strain, with a homofermentative metabolism giving rise to the production of lactic acid.

Preferably, it is a *Lactobacillus plantarum* which is resistant to pepsin under acidic pH conditions (about at least 95% of the bacteria are still alive after 40 minutes of treatment).

More particularly, the *Lactobacillus plantarum* used according to the invention exhibits good resistance to pancreatin (about at least 79% of the bacteria are still alive after 40 minutes of treatment).

Advantageously, the *Lactobacillus plantarum* used according to the invention exhibits good resistance to bile salts.

The *Lactobacillus plantarum* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), γ-interferon (γ-IFN) and tumour necrosis factor α (TNFα). On the other hand, the *Lactobacillus plantarum* used according to the invention induces little or no secretion of interleukins 12 (IL12) using this same test.

The *Lactobacillus plantarum* used according to the invention is *Lactobacillus plantarum* PTA-4799. This *Lactobacillus plantarum* strain was deposited according to the Treaty of Budapest at the American Type Culture Collection where it is recorded under the deposit number PTA-4799.

One embodiment of the composition according to the invention is a bacterial composition comprising *Lactobacillus plantarum* PTA-4799.

The composition made of probiotic bacteria according to the invention may also comprise at least one *Lactobacillus salivarius* strain.

The *Lactobacillus salivarius* strain used according to the invention is a Gram-positive strain. Advantageously, it is a catalase-negative strain, with a homofermentative metabolism giving rise to the production of lactic acid.

More particularly, the *Lactobacillus salivarius* used according to the invention exhibits good resistance to pancreatin (at least 100% of the bacteria are still alive after 40 minutes of treatment).

The *Lactobacillus salivarius* used according to the invention can induce the secretion of cytokines. This detection of the induction of cytokines was made by means of a test for in vitro stimulation of isolated peripheral blood mononuclear cells (PBMC). Among the cytokines induced during this test, there may be mentioned interleukins 10 (IL10) and tumour necrosis factor α (TNFα). On the other hand, the *Lactobacillus salivarius* used according to the invention induces little or no secretion of interleukin 12 (IL12) and γ-interferon (γ-IFN) using this same test.

The *Lactobacillus salivarius* used according to the invention is *Lactobacillus salivarius* PTA-4800. This *Lactobacillus salivarius* strain was deposited according to the Treaty of Budapest at the American Type Culture Collection where it is recorded under the deposit number PTA-4800.

One embodiment of the composition according to the invention is a bacterial composition comprising *Lactobacillus salivarius* PTA-4800.

The composition made of probiotic bacteria according to the invention may also comprise at least one *Lactobacillus paracasei* strain.

The *Lactobacillus paracasei* used according to the invention is a Gram-positive strain. Advantageously, it is a catalase-negative strain, with a homofermentative metabolism giving rise to the production of lactic acid.

Preferably, it is a *Lactobacillus paracasei* exhibiting poor resistance to pepsin, under acidic pH conditions (about at least 17.5% of the bacteria are still alive after 40 minutes of treatment).

More particularly, the *Lactobacillus paracasei* used according to the invention exhibits a very good resistance to pancreatin (about at least 100% of the bacteria are still alive after 40 minutes of treatment).

Advantageously, the *Lactobacillus paracasei* used according to the invention exhibits good tolerance to bile salts.

The *Lactobacillus paracasei* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), γ-interferon (γ-IFN) and tumour necrosis factor α (TNFα). On the other hand, the *Lactobacillus paracasei* used according to the invention induces little or no secretion of interleukins 12 (IL12) using this same test.

The *Lactobacillus paracasei* used according to the invention is *Lactobacillus paracasei* PTA-4798. This *Lactobacillus paracasei* strain was deposited according to the Treaty of Budapest at the American Type Culture Collection where it is recorded under the deposit number PTA-4798.

One embodiment of the composition according to the invention is a bacterial composition comprising *Lactobacillus paracasei* PTA-4798.

The composition made of probiotic bacteria according to the invention may also comprises at least one *Bifidobacterium bifidum* strain.

The *Bifidobacterium bifidum* strain used according to the invention is a Gram-positive strain. Advantageously, it is a catalase-negative strain, with a heterofermentative metabolism giving rise to the production of lactic acid and acetic acid.

The *Bifidobacterium bifidum* used according to the invention is *Bifidobacterium bifidum* PTA-4801. This *Bifidobacterium bifidum* strain was deposited according to the Treaty of Budapest at the American Type Culture Collection where it is recorded under the deposit number ATCC PTA-4801.

One embodiment of the composition according to the invention is a bacterial composition comprising *Bifidobacterium bifidum* PTA-4801.

The composition made of probiotic bacteria according to the invention may also comprises at least one *Bifidobacterium lactis* strain.

The *Bifidobacterium lactis* used according to the invention is a Gram-positive strain. Advantageously, it is a catalase-negative strain, with a heterofermentative metabolism giving rise to the production of lactic acid and acetic acid. The *Bifidobacterium lactis* strain used according to the invention is a Gram-positive, non-sporeforming, pleomorphic rod that possesses the ability to grow in milk, is moderately tolerant to exposure to oxygen, and has white to off-white circular, convex colonies with entire to erose edges when grown on the surface of MRS agar containing 0.05% cysteine.

The *Bifidobacterium lactis* strain used according to the invention is *Bifidobacterium lactis* PTA-4802. This Bifidobacterium lactis strain was deposited according to the Treaty of Budapest at the American Type Culture Collection on Nov. 15, 2002 for the purpose of patent procedures where it is recorded under the deposit number ATCC PTA-4802. The *Bifidobacterium lactis* strain PTA-4802 has the following probiotic attributes:

TABLE I

| Probiotic Attribute | PTA-4802 | |
|---|---|---|
| Strain Origin | Human | |
| Acid tolerance | ++++ | 89% |
| Bile Tolerance | +++ | 88% |
| Adherence[1] | | |
| Caco-2[2] | +++ | |
| Ht-29[3] | ++ | |
| Antibiotic Sensitivity[4] | | |
| B-lactam (gm+/−, anaerobes) | | |
| Amoxicillin | S | |
| Ampicillin | S | |
| Cephalothin | | |
| Cloxacillin | S | |
| Dicloxacillin | S | |
| Imipenem | R | |
| Penicillin G | S | |
| Cephalosporin (gm +/−) | | |
| Ceftazidime | S | |
| Quinolones (broad gm−, some g+) | | |
| Ciprofloxacin | R | |
| Nalidixic acid (g - only) | | |
| Macrolides (gm−/+, atypicals) | | |
| Clindamycin | I | |
| Erythromycin | I | |
| Miscellaneous Abs | | |
| Chloramphenicol | I | |
| Fusidic Acid (G - only) | | |
| Linezolid | | |
| Nitrofurantoin (UTI's) | R | |
| Novobiocin | | |
| Rifampicin | S | |
| Spectinomycin | | |
| Vancomycin | S | |
| Streptogramins | | |
| Quinopristin/dalfopristin | | |
| Aminoglycosides (broad g−) | | |
| Gentamicin | R | |
| Kanamycin | R | |
| Neomycin | R | |
| Streptomycin | R | |
| Polypeptide | | |
| Polymyxin B (topical, G- only) | R | |
| Tetracyclines | | |
| Tetracycline | R | |
| Trimethoprim-Sulfamethoxazole | | |
| Sulfamethoxazole (inactive for anaerobes) | R | |
| Trimethoprim | R | |
| L/D Lactate Production | 100/0 | |
| Pathogen Inhibition[5] | | |
| C. difficile | NA | |
| E. coli | +++ | |
| Listeria monocytogenes | + | |
| Salmonella typhimurim | + | |
| Staphylococcus aureus | + | |
| Beta-galactosidase Activity[6] | 985 | |

TABLE I-continued

| Probiotic Attribute | PTA-4802 |
|---|---|
| (Miller Units) | |
| Beta-galactosidase Activity | ++++ |
| Casein Digesting Capability[7] | |
| α-Casein Hydrolysis | + |
| β-Casein Hydrolysis | + |
| Whey Protein Digesting Capability[8] | |
| α-lactalbumin Hydrolysis | ++ |
| β-lactalbumin Hydrolysis | ++ |
| Bovine Serum Albumin | +++ |

1
Adherence Methodology:
Cells were grown O/N (1%) in 10 ml appropriate medium: washed 1× in 10 ml medium and resuspended in 6 ml medium; suspension adjusted to OD590 (0.5 to 0.54) These cells were mixed 1:1 with cell culture medium and 300 ul cell mix applied to each well containing confluent Caco-2 or HT-29 cells (cell mix also plated to determine cfu/ml). Let bacteria adhere to Caco-2 or HT-29 cells for 1.5 hr @ 37° C. Wash each well 3× with 1 ml PBS; fix with 1 ml metlanol; wash with1 ml water; Gram stain.
Adherence Scoring System:
The subjective scoring is based on microscopic counts in comparison with NCFM which was arbitrarily assigned a score of +++. All other cultures were compared against that score.
The numbers for Caco-2 and HT-29 adherence are actual values determining by counting 10 random fields on the sldie to give a total count (for 10 fields), divided by 10 for an average. THe variability for these can be high as sometimes fields will have 5 cells, and another field on the slide as 30, or 100. So, that is why 10 or more fields are counted randomly and both scores provided.
Scoring for Caco-2 and HT29  Adherence
Score        Adherent cells/Caco-2 or HT-29 cell

| X | 10 or less |
|---|---|
| XX | 10–20 |
| XXX | 21–50 |
| XXXX | 51–100 |
| XXXXX | 101–above |

2
Average of 36 cells of PTA-4802 per field of CaCO-2 cells (which can vary from 5–50 per field).
3
Average of 17 cells of PTA-4802 per field of HT-29 MTX cells (which can vary from 5–50 per field).
4
Antibiotic Sensitivity Profile
a. MICs were tested following NCCLS M11-A5 Reference Agar Dilution Procedure (Wadsworth Method) using MRS + cysteine Agar.
MIC >64 ug/ml = Resistant (R)
MIC 16–32 ug/ml = Intermediate (I)
MIC <4 ug/ml = Sensitive (S)
b. E-Strip on WC agar, internal to Niebull.
c. Disc diffusion method, Zhou et al.
5
Pathogen Inhibition Methodology
Producer strains spotted onto MRS agar, Incubated overnight at 37° C. then overlayed with semisolid agar containing indicator pathogens. All pathogens seeded in BHI soft agar, except C, albicans which was grown and seeded in 0.3% YE, 0.3% malt extract, 0.5% peptone, and 1.0% glucose.
Scoring for Pathogen Inhibition
Score        Characterization of zone of inhibition

| X | <5 mm diffuse |
|---|---|
| XX | >6 mm diffuse |
| XXX | <5 mm defined |
| XXXX | 6–10 mm defined |
| XXXXX | Acid cleared |

6
Beta-galactoside Activity
5-star scoring system

| + | 0–250 Miller Units |
|---|---|
| ++ | 251–500 Miller Units |
| +++ | 501–750 Miller Units |
| ++++ | 751–1000 Miller Units |

TABLE I-continued

| Probiotic Attribute | PTA-4802 |
|---|---|

+++++ 1001–> Miller Units
7
Casein Digesting Capability
100 mg of cells were added to a 5% suspension of casein at pH7, 100 mM phosphate buffer and hydrolysis performed at 35° C. for 24 hours, HPLC used a C4 column and detection at 214 nm.
8
Whey Protein Digesting Capability
1. Each Signma protein standard was dissolved to a concentration of 3 mg per ml with phosphate buffer, 60 mgs, and total volume 20 mls.
2. Each lyophilized probiotic strain was resuspended in the same phosphate buffer at a 10% (w/v) concentration. (1.0 g in 10 mls of buffer).
3. To 2 ml of the protein standard solutions (step 1) was added 1 ml (i.e. 100 mgs of cells) from the cell suspension (step 2). For a total reaction volume of 3 ml and final concentrations of 2 mg per ml protein and 33 mg per ml cells. Reaction vessels (5 ml, bijou, Sterilins) were mixed and then placed at 35° C. for 24 hours.
4. At 6 and 24 hours the vessels were re-mixed: a 1.5 ml sample was then taken, centrifuged (Eppendorf micro-centrifuge 13,000 rpm for 15 minutes) and then filtered (0.22 μm nylon).
5. Samples were stored frozen at −20° C. prior to analysis by HPLC.
6. HPLC was performed using a Phenomenex C18 "Aqua" column 250 × 4.6 mm (5μ, 200A) at 28° C. with a reverse phase water and acetonitrile (0.1% TFA) gradient. UV detection at 214 nm. Elution rate- 1 ml per minute 40 minutes run time per sample.

TABLE II

| Probiotic Attribute (ProSafe Testing)[9] | PTA-4802 |
|---|---|
| ProSafe Strain Code | MB007 |
| ProSafe Identification | B. animalis subsp. lactis |
| Antibiotic Sensitivity | MIC |
| B-lactam (gm +/−, anaerobes) | |
| Ampicillin | 0.125 |
| Pencillin G | 0.125 |
| Ampicillin/Sublactam | 0.125 |
| Glycopeptides | |
| Teicoplanin | ±0.125 |
| Macrolides (gm −/+, atypicals) | |
| Clindamycin | ±0.032 |
| Erythromycin | 0.063 |
| Miscellaneous Abs | |
| Chloramphenicol | 2 |
| Fusidic Acid (G - only) | 8 |
| Linezolid | NT |
| Vancomycin | 0.25 |
| Streptogramins | |
| Quinopristin/dalfopristin | ≦0.032 |
| Aminoglycosides (broad g-) | |
| Gentamicin | 64 |
| Streptomycin | 64 |
| Tetracyclines | |
| Oxytetracycline | 4 |
| Trimethoprim-Sulfamethoxazole | |
| Sulfamethoxazole (inactive for anaerobes) | ≦0.25 |
| Trimethoprim | ≦0.25 |
| PROSAFE Methods - See Methods Worksheet | |
| Recovery and Purity | 1 |
| Identification | 2D |
| Antibiotic Susceptibility | 3A–B, D |
| Resistance | |

TABLE II-continued

| Probiotic Attribute (ProSafe Testing)[9] | PTA-4802 |
|---|---|
| Acquired (Based on Cut-Off Values) | None |
| Detected Resistance Genes | None |
| ProSafe Antibiotic Cut-Offs | Cut-Off |
| B-lactam (gm +/−, anaerobes) | |
| Ampicillin | ≦0.5 |
| Pencillin G | ≦0.5 |
| Ampicillin/Sublactam | ≦0.5 |
| Glycopeptides | |
| Teicoplanin | Inconc |
| Macrolides (gm −/+, atypicals) | |
| Clindamycin | Inconc |
| Erythromycin | |
| Miscellaneous Abs | |
| Chloramphenicol | ≦4 |
| Fusidic Acid (G - only) | ≦16 |
| Linezolid | |
| Vancomycin | ≦1 |
| Streptogramins | |
| Quinopristin/dalfopristin | ≦0.25 |
| Aminoglycosides (broad g-) | |
| Gentamicin | ≦256 |
| Streptomycin | ≦256 |
| Tetracyclines | |
| Oxytetracycline | Inconc |
| Trimethoprim-Sulfamethoxazole | |
| Sulfamethoxazole (inactive for anaerobes) | Inconc |
| Trimethoprim | Inconc |

9
PROSAFE
METHODS
1. Recovery and purity check
Lactic acid bacteria were recovered on MRS agar or in MRS broth (Oxoid CM361), and incubated anaerobically at 37° C. for 1 to 4 days.
2. Identification
2A: AFLP and cluster analysis
AFLP is a PCR-based technique for whole-genome DNA fingerprinting by the selective amplification of restriction fragments (Janssen et al., Microbiology 142: 1881–1893, 1996). DNA was prepared using the method of Gevers et al. 9Gevers, D., G. Huys, and J. Swings. Applicability of rep-PCR fingerprinting for identification of Lactobacillus species. FEMS Microbiol. Lett. 205, 31–36, 2001). Two restriction enzymes, a 4-base cutter and a 6-base cutter digested purified total DNA.Adaptors were ligated to the appropriate 'stick end'of the restriction fragments and serve as binding sites for PCR primers. Selective amplification was performed with the primers containing at their 3'-end one 'selective base' that extends beyond the restriction site into the fragment. PCR products were separated according to their length on a high-resolution polyacrylamide gel using a DNA sequencer (ABIRPISM 377).
Fragments that contain an adaptor specific for the restriction half site created by the 6-bp cutter were visualized due to the 5'-end labeling of the corresponding primer with the fluorescent dye 6-FAM. The resulting electrophoretic patterns were tracked and normalized using the GeneScan 3.1 software (Applera, USA). Normalized tables of peaks, containing fragments of 50 to 536 base pairs, were transferred into the BioNumerics™ 3.5 software (Applied Maths, Belgium).For numerical analysis, data intervals were delineated between the 75- and 500-bp bands of the internal standard. Clustering of the patterns was done using the Dice coefficient and the UPGMA algorithm. The profiles were compared with the reference profiles of the lactic acid bacteria taxa as currently available in our database.
Following restriction enzymes and adaptors were used:
Hexacutter: EcoRI
Adaptor: 5'CTCGTAGACTGCGTACC-3' 3'-CTGACGCATGGTTAA-5'
Tetracutter: TagI
Adaptor: 5'-GACGATGAGTCCTGAC-3' 3'-TACTCAGGACTGGC-5'

TABLE II-continued

Probiotic Attribute (ProSafe Testing)[9]   PTA-4802

Primer combination:
E01: 5'-GACTGCGTACCAATTCA-E'
T01: 5'-CGATGAGTCCTGACCGAA-E'
2B, rep-PCR fingerprinting and cluster analysis
Cells were cultivated for 24 h in MRS at 37° C. and harvested from the fermentation liquor by centrifugation at 130000 rpm, 15 min and total DNA was extracted before (Gevers, D., G. Huys, and J. Swings. Applicability of rep-PCR fingerprinting for identification of Lactobacillus species. FEMS Microbiol. Lett. 205, 31–36, 2001). Rep-PCR fingerprinting was performed as described by Versalovic et al. (Versalovic J., M. Schneider, F.J. de Bruijn, and J.R. Lupski.Genomic fingerprinting of bacteria using repetitive sequence-based polymerase chain reaction. Methods in Molecular and Cell Biology 5, 25–40, 1994) and as modified by Gevers et al., 2001).
PCR amplifications were performed with (GTG)5(5'-GTGGTGGTGGTG-GTG-3') as primer. The PCR products were electrophoresed in an agarose gel. The rep-PCR profiles were visualized after staining with ethidium bromide under ultraviolet light, followed by digital image capturing using a CCD camera. The resulting fingerprinting were analyzed using the BioNumerics V2.0 software package (Applied Maths, Ghent, Belgium). The similarity among digested profiles was calculated using the Pearson correlationand an average linkage (UPGMA) dendrogram was derived from the profiles.
2C. ID-protein gel electrophoresis (SDS-PAGE) and cluster analysis
The preparation of the cell extracts and the protein gel electrophoresis were carried out in accordance with the protocol established by the Research Group of the Laboratory for Microbiology, University Ghent (Pot, B., Vandamme, P., Kersters, K.: Analysis of electrophoretic whole-organism protein fingerprints. Chemical Methods in Prokaryotic Systematics, M. Goodfellow, and A.G. O'Donnell (eds.). J. Wiley and sons, Chichester, 1994). The normalized and digitized protein patterns were numericallyanalyzed and clustered with the reference profiles in the 'LAB' database as currently available
2D. Box PCR
Cells were cultivated for 24 h in MRS at 37° C. and harvested from the fermentation liquor by centrifugation at 130000 rpm, 15 min and total DNA was extracted before (Gevers, D., G. Huys, and J. Swings. Applicability of rep-PCR fingerprinting for identification of Lactobacillus species, FEMS Microbiol. Lett. 205, 31–36, 2001). Rep-PCR fingerprinting was performed as described by Versalovic et al. (Versalovic J., M. Schneider, F.J. de Bruijn, and J.R. Lupski. Genomic fingerprinting of bacteriausing repetitive sequence-based polymerase chain reaction. Methods in Molecular and Cellular Biology 5, 25–40, 1994) and as modified by Gevers et al., 2001) PCR amplifications were performed with the BOX primer BOXAIR (5'-CTACGGCAAGGCGACGCTGACG-3') was used (Masco, L., G. Huys, D. Gevers, L. Verbrugghen, and J. Swings. Identification of Bifidobacterium species using rep-PCR fingerprinting. Sust. Appl. Microbiol. 26, 557–563, 2003).
The PCR products ere electrophoresed in an agarose gel. The BOX-PCR profiles were visualized after staining with ethidium bromide under ultraviolet light, followed by digital image capturing using a CCD camera. The resulting fingerprints were analyzed using the BioNumerics V2.0 software package (Applied Maths, Ghent, Belgium). The similarity among digested profiles was calculated using the Pearson correlation and an average linkage (UPGMA) dendrogram was derived from the profiles.
2E. Partial 16S rDNA sequence analysis and phylogenetic study
Genomic DNA was prepared according to the protocol of Niemann et al. (Niemann S., Puehler A., Tichy H.-V., Simon R., and W. Selbitschka, 1997. Evaluation of the resolving power of three different DNA fingerprinting methods to discriminate among isolates of a natural Rhizobium meliloti population. J. Applied Microbiology 82:477–484).
16s rRNA genes were amplified by PCR using the following primers:
16F27 (pA) 5'AGAGTTTGATCCTGGCTCAG3' position 8–27
16R1522 (pH) 5'AAGGAGGTGATCCAGCCGCA3' position 1541–1522
F: forward primer / R: reverse primer; Hybridizing position referring to E. coli 16R rRNA gene sequence numbering
PCR amplified 16S rDNAs were purified using the NucleoFast ® Terminator Cycle Sequencing Kit (Macherey-Nagel, Duren, Germany). Sequencing reactions were performed using the BidDye ® Terminator Cycle Sequencing Kit (Applied Biosystems, Foster City, CA, USA) and purified using the Montage ™ SEQ96 Sequencing Reaction Cleanup Kit (Millipore, Bedfore, MA, USA). Sequencing was performed using an ABI Prism ® 3100 Genetic Analyzer (Applied Biosystems, Foster City, CA, USA).
The following forward and two reverse primers were used to get a partial overlap of sequences, ensuring highly reliable assembled data:
16F358 (*Gamma) 5' CTC-CTACGGGAGGCAGCAGT 3'
position 339358
16R339 (Gamma) 5' ACTGCT-GCCTCCCGTAGGAG 3' position 358–339
F: forward primer / R: reverse primer; Hybridizing position referring to E. coli 16R rRNA gene sequence numbering
Sequence assembly was performed by using the program AutoAssembler ™ (Applied Biosystems, Foster City, CA, USA). Phylogenetic analysis was performed using the software package BioNumerics (Applied Maths, Belgium) after including the consensus sequence in an alignment of small ribosomal subunit sequences collected from the international nucleotide sequence library EMBL. This alignment was pairwise calculated using an open gap penalty of 100% and a unit gap penalty of 0%. A similarity matrix wascreated by homology calculation with a gap penalty of 0% and after discarding unknown bases. A resulting tree was constructed using the neighbor-joining method.
3. Antibiotic susceptibility testing
3A. Antibiotics
Susceptibility to the following antibiotics was tested: penicillin, ampicillin/sulbactam, gentamicin, and streptomycin (including high-level resistance), vancomycin, teicoplanin, guinupristin/dalfopristin, erythromycin, clindamycin, oxytetracycline, chloramphenicol, fusidic acid, trimethoprim, sulfamethoxazole/trimethoprim, linezolid.
3B. Bifidobacteria
LSM broth supplemented with cystein (0.3 g/l) served as nutrient medium for the MIC determinations of Bifidobacterium species in the pre-made micro titer plates. For the inoculation of these plates the test strains were freshly cultivated on modified Columbia agar* under anaerobic conditions (e.g., by AnaeroGen ™, Oxiod) and at 37° C. for 48 h. Single colonies of the corresponding strains were suspended in 5 ml saline up to an optical density of McFarland 0.5 standard. 10 µl of a 1:15dilution of this suspension in saline served as inoculum of the bifidobacteria in the microtiter plates: about 105 bacteria/ml. The inoculated MIC test plaes were then incubated at 37° C. in an anaerobic atmosphere for 48 h and the MICs were read as described before.
*Modified Columbia Agar (pH 6.7; g/l aqua dest.):
Columbia Agar Base (e.g., CM331, Oxoid): Supplementation with:

| | | | |
|---|---|---|---|
| Special peptone | 23.0 | Glucose | 5.0 |
| Soluble starch | 1.0 | Cystein hydrochloride | 0.3 |
| NaCl | 5.0 | | |
| Agar | 10.0 | | |

Kiare et al., 2005, Applied and Environmental Microbiology (accepted))
3C. Lactobacillus/Lactococcus

TABLE II-continued

| Probiotic Attribute (ProSafe Testing)[9] | PTA-4802 |
|---|---|
| The inocula of the strains of Lactobacillus and Lactococcus species were prepared by suspending several freshly cultivated single colonies in a tube with 5 ml of saline up to an optical density of McFarland standard No. 0.5. The corresponding colonies were picked up from MRS (de Man, Rogosa, Sharpe) agar plates on which the strains were grown for 48 h at 37° C. and at 5% CO2 atmosphere. Subsequently, this suspension was diluted 1:10 by transferring 4 ml of the McFarland No. 0.5 suspension into asuitable inoculum container with 36 ml of saline and subsequent careful mixing. The MIC microtiter test plates (95 wells with different concentrations of the test antibiotics and one well for the growth control without any antibiotic) were prepared before. Nutrient medium: LSM (lactobacilli susceptibility test medium) broth consisting of 90% Iso-sensitest broth plus 10% MRS broth (pH 6.7). The inoculations of the pre-made MIC test plates were performed by a multi-point inoculator (final inoculum of these LAB in the microtiter plate: about 105 bacteria/ml). The plates were subsequently incubated in ambient air or in a 5% CO2 atmosphere at 37° C. for 24(-48) h. The MICs were read as the lowest concentration inhibiting the growth of the test organism. (Klare et al., 2005. Applied and Environmental Microbiology (accepted)) 3D. Microbiological cut-offs Cut-offs defined on the basis of MIC distribution among a specific taxonomic group of the PRSF strain collection. The ultimate aim to define "microbiological" cut-offs instead of "clinical or pharmacokinetic/pharmacodynamic" cut-offs was to distinguish among "intrinsic" and "acquired" resistance traits. Depending on the taxonomic group studied, these cut-offs were specified at the genus or species level. A minimum number of 10 strains of the same species is required to set microbiological cut-off values. However, for some of the species this number was not available in the PROSAFE collection. The antibiotic susceptibility results for these strains are mentioned as "no cut-off values defined." Types of Resistance Intrinsic Resistance: Natural or inherent resistance that is present in the wild type population of a given taxonomic group Acquired Resistance: Type of resistance present in strains with MICs that are higher than the normal range of the MIC distribution of the wild type population of a given taxonomic group. This resistance usually originates from gene mutations or recombinations.Inconclusive: Due to insufficient information available, no clear distinction between intrinsic and acquired resistance can be made at this moment. | |

One embodiment of the composition according to the invention is a bacterial composition comprising *Bifidobacterium lactis* PTA-4802.

Another embodiment of the composition according to the invention is a bacterial composition comprising at least one strain selected from the group consisting of *Lactobacillus acidophilus* PTA-4797, *Lactobacillus plantarum* PTA-4799, and *Bifidobacterium lactis* PTA-4802.

More particularly, the composition according to the invention may comprise at least 2 strains selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

More particularly, the composition according to the invention may comprise 3 strains selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

Preferably, the composition according to the invention may comprise a blend of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium lactis* PTA-4802 and *Bifidobacterium bifidum* PTA-4801.

The composition according to the invention may be used in the form of a bacterial suspension, before or after freezing, or of a freeze-dried powder. Indeed, regardless of the form used, the composition may be frozen.

The relative proportion of each bacterium in the composition can vary in large limit for example from 1/99 to 99/1 in the case there is at least 2 strains.

The composition according to the invention may comprise from $10^6$ to $10^{11}$ CFU of bacteria/g of composition, and more particularly from $10^8$ to $10^{11}$ CFU of bacteria/g of composition. The term CFU means "colony forming units". The expression gram of composition is understood to mean the food product or pharmaceutical preparation, and preferably $10^9$ to $10^{11}$ CFU/g if in a freeze-dried form.

The composition according to the invention is useful for the treatment, the primary prevention or the recurrence, and also the prevention and/or the reduction of inflammatory bowel disease.

The bacterial composition according to the invention is also useful for maintaining the homeostasis of the immune system.

The bacterial composition according to the invention is also useful for the prevention and/or the reduction of allergenicity.

The bacterial composition according to the invention is also useful as immunoadjuvent.

An other subject of the invention is also an immunomodulation method comprising the step of using at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

The composition according to the invention may be used in the form of a food product or pharmaceutical preparation.

The expression pharmaceutical preparation is understood to mean for example a preparation in the form of capsule or tablet.

The subject of the invention is also a food, dietary supplement or pharmaceutical composition comprising the bacterial composition described above.

Preferably, the food composition comprising the composition according to the invention is a food supplements, a beverage product or a milk base powder.

More particularly, the food composition comprising the composition according to the invention is a dairy product.

More preferably the food composition comprising the composition according to the invention is an infant formula.

The food or pharmaceutical composition according to the invention may have immunomodulation properties.

Another subject of the invention is also the use of this composition in the preparation of a carrier administered to humans or to animals for a therapeutic or prophylactic purpose in the gastrointestinal system.

The invention provides also a pharmaceutical composition comprising the bacterial composition described above useful for the prevention of inflamatory bowel disease.

The invention provides also a pharmaceutical composition comprising the bacterial composition described above useful for immunomodulation.

The FIGS. 1, 3 and 5 are schedules of injection.

The FIGS. 2, 4 and 6 are Wallace and Ameho scores, and weight of loss.

Concrete but nonlimiting examples of the invention will now be described.

EXAMPLES

1/PBMC Test

PBMC (Peripheral Blood Mononuclear Cells) are prepared by centrifugation from human blood, derived from known donors and is further purified on a Ficoll gradient. Cells are harvested, washed, (red blood cells removed) and counted.

Bacteria are prepared according to standard conditions and counted by plating on agarose medium according to proper dilutions ($10^{-7}$, $10^{-8}$, $10^{-9}$ in Ringer solution).

Cells are washed 3 times and suspended (et non dissolved) in PBS buffer. A verifier par Dominique PBMC cells are stimulated for 48 hours with the bacteria (allow negative control with Phosphate Buffer Saline solution (PBS)) under appropriate conditions of $CO_2$. Then the supernatant containing the cytokines is frozen at $-20°$ C.

Cytokines expression levels are determined by ELISA tests (<<Enzyme linked immuno sorbent assay >>). ELISA plates are coated with anti-cytokine antibody (overnight procedure) and the antibody is blocked with a surfactant, the tween 80.

A proper standard is prepared for known concentrations of cytokines which will cover the detection range of 15.62 till 2000 pg/ml (incubate overnight). Perform the anti-cytokine detection and quantify with streptavidine reaction on substrate (10 mg dABTS/10 ml of citric acid buffer 0.1M, pH4.35/20 µl H2O2).

Cytokines are either pro-inflammatory/Th1 (TNFα, IFNγ, IL12) or anti-inflammatory (IL10).

| Strains | IL-10 | IL-12 | IFN-γ | TNF-α |
|---|---|---|---|---|
| L. acidophilus PTA-4797 | 309 | | 1970 | 27591 |
| L. salivarius PTA-4800 | 6881 | 31 | 1148 | 23509 |
| L. paracasei PTA-4798 | 300 | 31 | 921 | 14046 |

The values are pg/ml.

2/Preparation of a Composition Made of Lactobacillus acidophillus PTA-4797, Lactobacillus plantarum PTA-4 799 and Bifidobacterium lactis PTA-4802

A blend of 3 strains is prepared containing *Lactobacillus acidophilus* PTA-4797, *Lactobacillus plantarum* PTA-4799, et *Bifidobacterium lactis* PTA-4802. This blend is named LAB.

To show in vivo, the immuno modulation capacity of this blend according to the invention, animal test were performed aimed at decreasing the chemically induced gut inflammation of mice. Several models were set-up to mimic human inflammatory bowel diseases.

In the first model, injections of 1 mg/mice of TNBS (trinitrobenzène sulfonic acid, which is a colitis inducing agent) on days 0, 7 and 14, and 2 mg/mice of TNBS on day 20 (double dose) will evoke a chronic colitis. The schedule of injection is drawn on FIG. 1. The intake of bacteria (LAB) on days −4 to −1, 6, 9, 13 and 19 will show macroscopic and histological effects, which are scored on day 22, according to standart scores (Wallace and Ameho respectively).

The results obtained (see FIG. 2) clearly showed an improvement of the colitis symptoms evidenced by
reduction of the increase of the submucosa
reduction of the inflammation
less weight loss A second model of chronic colitis was also used (based on Camoglio et al., Eur J Immunol 2000), 2 mg/mice of TNBS injected by intra-rectal route on days 0, 7, and 14 induce a serious chronic colitis. The schedule of injection is drawn on FIG. 3. The intake of bacteria (LAB) on days −5 to −1, on days 5 and 12 (FIG. 3) will show macroscopic and histological effects, which are scored on day 16, according to standard scores (Wallace and Ameho respectively).

The results obtained clearly showed an improvement of the colitis symptoms evidenced (see FIG. 4) by
absence of necrotic lesions
reduction of the increase of the submucosa
reduction of the inflammation A third acute model of mice colitis was also set up. 100 mg/kg mice of TNBS is injected on day 0. This will evoke an acute colitis. The schedule of injection is drawn on FIG. 5. The intake of *Bifidobacterium lactis* PTA-4802 or *Lactobacillus plantarum* PTA-4799 ($10^7$ bacteria/mouse) on days −5 to 0 show macroscopic and histological effects which are scored on day 2.

Clear macroscopic improvement of the colitis symptoms were evidenced for strains *Bifidobacterium lactis* PTA-4802 and *Lactobacillus plantarum* PTA-4799 (FIG. 6).

In general all the TNBS-induced colitis models in mice show that feeding LAB to these mice significantly reduced the level of intestinal translocation of indigenous bacteria from the intestinal flora into mesenteric lymph nodes and spleen after the induction of colitis. In addition, no translocation of probiotic bacterial strains according to the invention was observed.

3/Resistance to Pepsin

The aim of this test is to evaluate the resistance of bacteria to the passage of the gastric barrier by determining the number of bacteria that survive after cultivation in the presence of a pepsin solution in acid environment. In short, 100 µl of a stock culture frozen at $-80°$ C. is inoculated in 10 ml of MRS (Man Rogosa Sharp) culture medium and incubated overnight at $30°$ C. or $37°$ C. Then cells are washed 3 times in PBS at pH7 and the pellet is suspended in 1 ml PBS buffered and inoculated in 200 µl aliquots in 4 tubes with 1 ml of filtered pepsin solution at pH 2 supplemented with 300 µl of NaCl (0.5%). Cell count is performed on 100 µl aliquots taken from the tubes incubated at T0 (time of inoculation), T0+5 min; T0+20 min; T0+40 min; T0+60 min and dilutions are plated on MRS (100 µl) of $10^{-5}$, $10^{-6}$ et $10^{-7}$ (consecutive 10 fold dilutions made in 1 ml Ringer solution). The percentage surviving bacteria is calculated for each incubation time from the reading of the dilution series.

All results displayed in the tables are the result of triplicate experiments

| Strains | 5 min | 20 min | 40 min | 60 min |
|---|---|---|---|---|
| L. acidophilus PTA-4797 | 91 | 74 | 73 | 55 |
| L. plantarum PTA-4799 | 100 | 100 | 95 | 42 |
| L. salivarius PTA-4800 | 100 | 66 | 23 | 7 |
| L. paracasei PTA-4798 | 100 | 17.5 | 17.5 | 1.5 |

Results as % of survival compared to T=0.

4/Resistance to Pancreatin

The aim of this test is to evaluate the resistance of bacteria to the passage of the intestinal transit by determining the number of bacteria that survive after cultivation in the presence of a pancreatin solution in basic environment. In short, 100 µl of a stock culture frozen at −80° C. is inoculated in 10 ml of MRS (Man Rogosa Sharp) culture medium and incubated overnight at 30° C. or 37° C. Cells are washed 3 times in PBS at pH7 and the pellet is suspended in 1 ml PBS buffered and inoculated in 200 µl aliquots in 4 tubes with 1 ml of filtered pancreatin solution at pH 8 supplemented with 300 µl of NaCl (0.5%). Cell count is performed on 100 µl aliquots taken from the tubes incubated at T0 (time of inoculation), T0+5 min; T0+20 min; T0+40 min; T0+60 min; T0+120 min and dilutions are plated on MRS (100 µl) of $10^{-5}$, $10^{-6}$, $10^{-7}$ (consecutive 10 fold dilutions made in 1 ml Ringer solution). The percentage surviving bacteria is calculated for each incubation time from the reading of the dilution series. All results displayed in the tables are the result of triplicate experiments.

| Strains | 5 min | 20 min | 40 min | 60 min | 120 min |
|---|---|---|---|---|---|
| L. acidophilus PTA-4797 | 83 | 100 | 100 | 170 | 170 |
| L. salivarius PTA-4800 | 100 | 115 | 152 | 158 | 155 |
| L. plantarum PTA-4799 | 86 | 72 | 79 | 84 | 87 |
| L. paracasei PTA-4798 | 65 | 100 | 100 | 100 | 100 |

Results as % of survival compared to T=0.

5/Resistance to Bile Salts

The experimental is procedure is as follows. 100 µl culture of a stock frozen at −80° C. is inoculated in 10 ml de milieu de culture MRS (Man Rogosa Sharp) and incubated overnight at 30° C. or 37° C. The optical density (OD) is measured and a dilution is prepared (OD=0.05 to 0.1) in two bottles. One of the culture bottles is supplemented with a 0.3% solution of bile salts (750 µl of a filtered 12% solution ) and incubated at the correct temperature. The OD is regularly measured until a OD of 0.3 is reached in the control bottle without bile salts. At that point the OD of the supplemented bottle is measured and one starts to measure the time needed to obtain the same OD of 0.3. The resistance of the strain is therefore evaluated as the delay in growth time.

Results are coded as sensitive (0; more than 60 minutes), tolerant (1; between 15 and 60 minutes) or resistant (2; less than 15 minutes).

All results displayed in the tables are the result of triplicate experiments

| Strains | Resistance |
|---|---|
| L. acidophilus PTA-4797 | 1 |
| L. plantarum PTA-4799 | 2 |
| L. paracasei PTA-4798 | 2 |

6/Hydrophobicity and Affinity for Organic Solvents

The MATS test as described by Rosdenberg et al., 1980 (FEMS Microbiol. Letters 9;29–33) has been used. In short the test measures (grown overnight under normal in vitro growth conditions and washed twice in PBS) the hydrophobicity and polarity of the bacterial cell wall, based on the repartition (measured by optical density) of the bacteria into two non mixable liquid aqueous phases and five respective solvents. Growth medium is MRS (Man Rogosa Sharp) and the aqueous phase is a buffer as PBS. The solvents were decane, hexadecane, ethyl acetate, chloroform and xylene.

The affinity for chloroform, acid solvent, reflects the electron donor nature of the bacterium (basic reaction)

The affinity for Ethyl Acetate, basic solvent, reflects the electron acceptor nature of the bacterium (acid reaction)

The affinity for apolar solvents (decane, hexadecane, xylene) reflects the hydrophobic character of the bacterium.

Possibly a high hydrophobicity is related to the presence of glycoproteins on the cell wall surface, while a low hydrophobicity could be linked to the presence of polysaccharides on the cell wall surface.

% D'hydrophobicity=(1−A/A0)×100 with

AO: Original OD at 540 nm (set more or less at OD=0,6 in PBS)

A: Optical density of aqeous phase (for 1 ml) after vortexing and stabilisation period

| Strains | Decane | Hexadecane | Ethylacetate | Chloroform | Xylene |
|---|---|---|---|---|---|
| L. acidophilus PTA-4797 | 81.9 | 60.4 | 44.2 | 90.3 | 90.9 |
| L. salivarius PTA-4800 | 23.02 | 38.17 | 2.25 | 79.28 | 51.18 |
| L. paracasei PTA-4798 | 36.5 | 37.4 | 28.8 | 45.2 | 30.6 |
| L. plantarum PTA-4799 | 25.3 | 25.6 | 28.7 | 28.8 | 21.9 |

The invention claimed is:

1. A bacterial composition having immunomodulation properties comprising *Bifidobacterium lactis* PTA-4802.

2. The bacterial composition according to claim 1 further comprising at least one additional strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, and *Bifidobacterium bifidum* PTA-4801.

3. The bacterial composition according to claim 1 further comprising at least two additional strains selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, and *Bifidobacterium bifidum* PTA-4801.

4. The bacterial composition according to claim 1 comprising a blend of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium lactis* PTA-4802, and *Bifidobacterium bifidum* PTA-4801.

5. The bacterial composition according to claim 1, comprising from $10^5$ to $10^{11}$ CFU of bactena/g of composition.

6. The bacterial composition according to claim 5, comprising from $10^8$ to $10^{11}$ CFU of bactenalg of composition.

7. A process for the prevention or the reduction of inflammatory bowel disease, comprising the step of administering to a human or an animal an efficient preventing or reducing amount of inflammatory bowel disease, of a bacterial composition as defined in claim 1.

8. A process for maintaining the homeostatis of the immune system comprising the step of administering to a human or an animal an efficient maintaining amount of the homeostasis of the immune system, of a bacterial composition as defined in claim 1.

9. A process for the prevention or the reduction of allergenicity comprising the step of administering to a human or an animal an efficient preventing or reducing amount of allergenicity, of a bacterial composition as defined in claim 1.

10. An immunoadjuvent composition, comprising a bacterial composition as defined in claim 1.

11. An immunomodulation method comprising the step of using *Bifidobacterium lactis* PTA-4802.

12. A food, dietary supplement or pharmaceutical composition comprising a composition as defined in claim 1.

13. The composition according to claim 12, being in the form of a dairy product.

14. The composition according to claim 13, being in the form of an infant formula.

15. The composition according to claim 13, having immunomodulation properties.

16. A pharmaceutical composition comprising the composition as defined in claim 1 for the prevention of inflammatory bowel disease.

17. A pharmaceutical composition comprising the composition as defined in claim 1 for immunomodulation.

18. The immunomodulation method according to claim 11, further comprising using at least one additional strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, and *Bifidobacterium bifidum* PTA-4801.

* * * * *